United States Patent [19]

Chu et al.

[11] Patent Number: 5,219,576

[45] Date of Patent: * Jun. 15, 1993

[54] COLLAGEN WOUND HEALING MATRICES AND PROCESS FOR THEIR PRODUCTION

[75] Inventors: George H. Chu, Sunnyvale; Yasushi Ogawa, Pacifica, both of Calif.; John M. McPherson, Hopkinton, Mass.; George Ksander, Redwood City, Calif.; Bruce Pratt, Union City, Calif.; Diana Hendricks, Brea, Calif.; Hugh McMullin, San Bruno, Calif.

[73] Assignee: Collagen Corporation, Palo Alto, Calif.

[*] Notice: The portion of the term of this patent subsequent to Aug. 21, 2007 has been disclaimed.

[21] Appl. No.: 801,732

[22] Filed: Dec. 3, 1991

Related U.S. Application Data

[62] Division of Ser. No. 630,299, Dec. 19, 1990, Pat. No. 5,110,604, which is a division of Ser. No. 213,726, Jun. 30, 1988, Pat. No. 5,024,841.

[51] Int. Cl.$^5$ ............................................. A61K 9/14
[52] U.S. Cl. .................................. 424/484; 424/422; 424/85.2; 424/85.4; 514/21; 514/801; 514/887
[58] Field of Search ............... 424/484, 422, 423, 427, 424/428, 85.4, 85.2; 514/2, 8, 21, 801, 887; 530/356, 399

[56] References Cited

U.S. PATENT DOCUMENTS 4,950,483  8/1990  Ksander ............................ 424/425
4,983,580  1/1991  Gibson ............................... 514/21

FOREIGN PATENT DOCUMENTS 0042253 12/1981 European Pat. Off. .
0154447  9/1985 European Pat. Off. .
0157359 10/1985 European Pat. Off. .
0171176  2/1986 European Pat. Off. .
0243179 10/1987 European Pat. Off. .
0013249  1/1980 Japan .

OTHER PUBLICATIONS

McPherson et al., *Collagen and Related Research Clinical and Experimental* (1988) 8(1):83–100.
Doillon et al., *J. Biomed. Mater. Res.* (1986) 20(8):1219–1228.

*Primary Examiner*—Thurman K. Page
*Assistant Examiner*—G. S. Kishore
*Attorney, Agent, or Firm*—Morrison & Foerster

[57] ABSTRACT

Collagen implants that are useful as wound healing matrices are characterized by being formed of collagen fibrils that are not chemically cross-linked, and having a bulk density of 0.01 to 0.3 g/cm$^3$ and a pore population in which at least about 80% of the pores have an average pore size of 35 to 250 microns. The implants are capable of promoting connective tissue deposition, angiogenesis, reepithelialization, and fibroplasia. The wound healing matrix also serves as an effective sustained delivery system for bioactive agents.

4 Claims, 2 Drawing Sheets

COLLAGEN WOUND HEALING MATRICES AND PROCESS FOR THEIR PRODUCTION

This application is a divisional application of U.S. application Ser. No. 07/630,299 filed Dec. 19, 1990, now a U.S. Pat. No. 5,110,604, which is a divisional application of U.S. application Ser. No. 07/213,726 filed Jun. 30, 1988, now a U.S. Pat. No. 5,024,841 to which applications we claim priority under 35 USC Section 120 and which applications are incorporated herein by reference in their entirety.

TECHNICAL FIELD

This invention is in the field of collagen chemistry and wound implants. More specifically, it relates to solid matrices of collagen that are useful as wound healing implants and sustained-release depots for administering bioactive agents, and processes for their preparation.

BACKGROUND

Wound healing implants should have the ability to adhere and conform to the wound site, and ideally should facilitate regrowth of epidermis, and accumulation of fibroblasts, endothelial cells, and wound healing regulatory cells into the wound site to speed healing (e.g., promotion of connective tissue deposition and angiogenesis). Whether a given implant can meet these objectives is a reflection of the chemical composition and physical characteristics of the implant.

Collagen, the major protein of connective tissue, has been used previously in wound dressings. Procedures for rendering xenogeneic collagen substantially nonimmunogenic are available. U.S. Pat. No. 4,412,947 describes an absorbent dressing having a bulk density of 0.005 to 0.0065 g/cm$^3$ made by freeze drying a dispersion of native collagen in a weak aqueous organic acid solution. Such dressings that are made from acid solution have tightly woven fibers with typically low absorptive capacity and pore sizes that do not encourage optimum cell ingrowth.

PCT Application no. 85/04413 describes a carbodiimide or succinimidyl ester cross-linked collagen sponge formed from a dispersion or solution of collagen that is dehydrated before or after the collagen is cross-linked by addition of the cross-linking agents. Collagen sponges made in this manner have similar disadvantages to those made from the freeze dried acid solution.

Other references describing collagen sponges are U.S. Pat. Nos. 3,742,955, 3,743,295, 3,810,473, 4,515,637, and 4,578,067.

The present invention is directed to providing collagen implants that are biocompatible, biodegradeable, and are capable of promoting connective tissue deposition, angiogenesis, reepithelialization, and fibroplasia. Another aspect of the invention is directed to providing a collagen matrix useful for sustained delivery of bioactive agents.

DISCLOSURE OF THE INVENTION

The present invention encompasses novel collagen implants that are useful as wound healing matrices, and processes for making those implants.

These collagen implants are characterized in that the collagen is biocompatible, biodegradeable, substantially nonpyrogenic, fibrillar, and not chemically cross-linked; and the implant has a bulk density of 0.01 to 0.3 g/cm$^3$, and a pore population in which at least about 80% of the pores are of a size sufficient to permit cell ingrowth.

The wound healing implant also serves as an effective sustained delivery vehicle for bioactive additives, such as heparin or other glycosaminoglycans, extracellular matrix proteins, antibiotics, and growth factors, for example, epidermal growth factor (EGF), platelet derived growth factor (PDGF), fibroblast growth factor (FGF), connective tissue activating peptides (CTAP), transforming growth factors (TGFs) and the like. By virtue of effectively delivering such bioactive factors, the implants of the invention are also useful in oncostasis, immunomodulation, osteogenesis, and hematopoiesis. Nonbioactive agents such as preservatives, antimicrobials, or dyes may also be incorporated into the implant.

The process for making the implants comprises the steps of:

a) providing an acidic aqueous solution of collagen;
b) precipitating the collagen from the solution by raising the pH of the solution, and forming a homogenous dispersion of the precipitated collagen fibrils;
c) casting the dispersion in a mold to a desired thickness;
d) flash-freezing the cast dispersion at a temperature below about $-20°$ C.; and
e) lyophilizing the frozen cast dispersion to form a substantially moisture-free collagen implant.

Optionally, bioactive additives can be added to the homogeneous dispersion at step (b) above, or immediately following step (b). Alternatively, one may soak the dried implant in a solution containing the bioactive agent, or by using a sterile pipet or dropper and dropping a solution containing the bioactive agent onto the dried implant.

Additional aspects of the invention include further steps in the above process such as compressing the implant to form implants having bulk densities in the upper portion of the above mentioned range and/or heat treating (curing) the implant to increase its tensile strength.

MODES FOR CARRYING OUT THE INVENTION

A. Preparation of Collagen Implants

Figure 1:
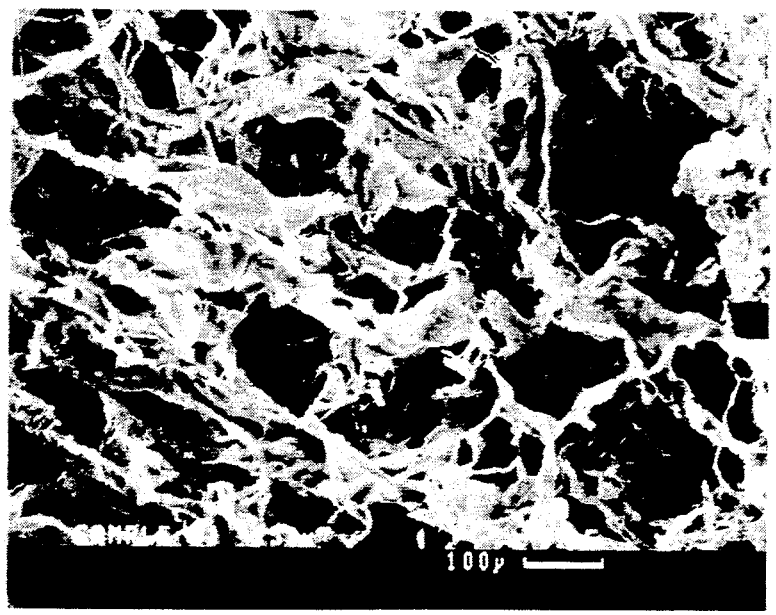
FIG. 1 is a scanning electron microscope photograph of a collagen implant of this invention illustrating its characteristic structure.

The present invention preferably employs collagen in solution (CIS) as a starting material. An acidic solution of an atelopeptide form of bovine skin collagen is commercially available from Collagen Corporation, Palo Alto, Calif., under the trademark Vitrogen ® 100. This material is a solution containing about 3 mg/ml of collagen at a pH of approximately 2.0. As indicated below, it is preferable to concentrate the Vitrogen ® 100 solution for use in the invention. Any solubilized form of collagen can, of course, be employed as a starting material, including bovine tendon collagen, human collagen, and the like.

The collagen used is not chemically cross-linked, e.g., by the addition of aldehydes or other chemical additives which react with the collagen to form covalent bonds. If desired, the collagen matrix may be heat-treated as described below: this may effect a form of covalent bonding, but does not require the addition of chemical cross-linking agents. Chemical cross-linking agents excluded from the invention are also distinguished from biological molecules which may have a non-covalent affinity for collagen, such as glycosaminoglycans, e.g., heparin. Such molecules which do not bind covalently in solution are within the scope of this invention.

The concentration of collagen in the starting solution can vary from about 2 to about 75 mg/ml. The concentration plays a part in the properties of the collagen implant product. Concentrations in the lower part of this range give products-having relatively low tear strengths that degrade more rapidly in aqueous environments. Higher concentrations in the range give denser, stronger implants which degrade slowly in aqueous environments. Preferred concentrations are in the range of about 4-20 mg/ml.

The concentration of collagen can be adjusted downwards, if necessary, by simple dilution. Upwards adjustments can be made using methods which do not damage the collagen such as by precipitating the collagen and redissolving it at the higher concentration.

In the process the collagen in solution is precipitated by raising the pH of the solution to approximately neutral pH or higher, such as by adding an alkaline buffer or the like to form a homogeneous dispersion of reconstituted fibrillar collagen. Typical buffers include inorganic (e.g. phosphate) and organic (e.g., acetate) buffers.

The homogeneous dispersion that results is cast into a sheet. With low collagen concentration dispersions, this can be done by merely pouring the dispersion into the casting zone. With more concentrated materials it may be helpful or necessary to spread the material with a blade or similar instrument to provide a uniform layer. The thickness of the cast layer of dispersion is generally from about 1 to about 20 mm thick, with thicknesses of from about 2 to about 8 mm being preferred.

The cast layer is then frozen under rapid or "flash freezing" chill conditions. If the freezing is slow and gradual, the size of the ice crystals formed in the layer will be large and the resulting final product will have inconsistent pore sizes. One typical flash-freezing method involves casting on a high heat conductivity surface, such as a metal surface, and then placing this high heat conductivity surface in intimate contact with a volume of chilled liquid or another chilled metal surface such that the heat is rapidly drawn from the cast layer. The temperature employed for this chilling is generally less than $-40°$ C., and preferably is less than $-50°$ C. and more preferably is in the range of from $-65°$ C. to about $-110°$ C.

The frozen layer is then lyophilized by methods known in the art. The lyophilization temperature is preferably as high as possible without permitting melting of the layer. In view of the dissolved collagen and accompanying salts and buffers in the fluid, $-5°$ C. is generally the highest nonmelting temperature, with temperatures of from about $-25°$ C. to about $-10°$ C. being preferred. Generally, temperatures below about $-30°$ C. give very slow rates of lyophilization. The vacuum employed for lyophilization can vary. Ultra-high vacuums are not required, however, with absolute pressures in the range of from about 0.01 torr to about 0.1 torr generally being employed. The time required to lyophilize the layer will depend upon the layer's thickness, but generally, times in the range of from about 4 hours to about 30 hours are employed. The actual times employed will depend upon the temperature and vacuum employed. After lyophilization, the layer will typically be substantially free of water (i.e., it contains less than about 25% by weight moisture, preferably less than about 10% by weight moisture). If necessary, the implant may be dried after the lyophilization to remove all water.

Additional optional steps may be added to the process to alter the properties of the resulting collagen implant. In one option, the process includes an additional step in which an inert gas is admixed with the collagen dispersion prior to casting. In this additional step an inert gas is suspended in the viscous collagen dispersion to produce a gas-in-semisolid dispersion. The type of inert gas used is not critical. Air is the usual gas of choice, but argon, nitrogen or any other gas which will not react with the collagen and which will not leave pharmacologically unacceptable residues in the final product can be used. The volume of gas incorporated into the collagen dispersion will range from about 0.33 to about 3 volumes per volume of dispersion. Preferably, the volume of gas is from about 0.5 to about 2 volumes per volume of dispersion.

The method of incorporating the gas into the dispersion must be a low shear method. A high speed blender or mixer is unacceptable as it will lead to physical degradation of the structure of the collagen. Suitable mixing methods include bubbling, sparging, or pumping the gas into the dispersion, shaking the two phases together, gently mixing the two phases with a paddle mixer, and the like. The gas-in-semisolid dispersion that results from the above-noted incorporation is then cast and processed as set forth above.

In another option, the implant is compressed to increase its bulk density. Compressed implants typically have bulk densities in the range of 0.05 to 0.3 g/cm$^3$, whereas noncompressed implants normally have bulk densities of 0.01 to 0.05 g/cm$^3$. Compression can be accomplished by passing a sheet of the product through a press, or through rollers or the like to achieve the desired degree of compression. Compression will also decrease the thickness of the implant.

In another variation of the above process, multilayer products can be formed by serially casting and flash freezing a plurality of layers and thereafter lyophilizing and drying. This variation can be useful to deposit a layer or "skin" of collagen on one or both sides of the implant without having to laminate the layers together. Such a skin is usually less than about a millimeter thick, such as from 0.1 mm to about 0.75 mm. In a typical embodiment, a 1 mm thick layer of a collagen dispersion having the characteristics of the dispersion used in the main process before gas addition is cast and flash frozen. Thereafter, the dispersion of fibrillar collagen with or without suspended gas is cast and flash frozen. This multilayer composite is then lyophilized.

When producing a multilayer material, it is generally preferred to cast and freeze the individual layers and then lyophilize the entire composite at once. The same conditions described for freezing the individual layers may be for multi-layer composites. Lyophilizing times and conditions generally are cumulated when applied to a composite material. Implants may be laminated with other biocompatible materials if desired.

In another variation of the process the dry (less than 10% by weight moisture) collagen implant is heat cured to increase its strength without affecting pore size or absorbency adversely. The curing will normally take place at atmospheric pressure or under vacuum at temperatures in the range of 60° C. to 120° C., preferably 75° C. to 90° C. Relative humidity during the curing step is kept below about 55%. The curing will normally take between 4 hr and one week and may be carried out in open or closed containers. The strength time (as defined in Example 4, infra) of the cured implants will normally be greater than about 20 secs, more normally greater than about 50 secs, depending on the thickness of the implant.

In still another option, glycosaminoglycans, bioactive agents, and/or non-bioactive agents are added to the collagen dispersion prior to flash-freezing and lyophilization. Alternatively, one may soak the dried implant in a solution containing the preferred additive, or by using a sterile pipet or dropper and dropping a solution containing the additive onto the dried implant.

The addition of bioactive agents or protein factors enhances the ability of the wound healing matrices to promote wound healing. One or more bioactive agents may be incorporated to promote granulation tissue deposition, angiogenesis, reepithelialization, and fibroplasia. Additionally, these and other factors are known to be effective immunomodulators (either locally or systemically), hematopoietic modulators, osteoinductive agents, and oncostatic agents (e.g., TGF-beta has been shown to exhibit all of these activities). The bioactive additives or protein factors used herein may be native or synthetic (recombinant), and may be of human or other mammalian type. Human FGF (including both acidic or basic forms), PDGF, and TGF-beta are preferred. Methods for isolating FGF from native sources (e.g., pituitary, brain tissue) are described in Bohlen et al, *Proc Nat Acad Sci USA*, (1984) 81:5364, and methods for isolating PDGF from platelets are described by Rainer et al, *J Biol Chem* (1982) 257:5154. Kelly et al, *EMBO J* (1985) 4:3399 discloses procedures for making recombinant forms of PDGF. Methods for isolating TGF-beta1 from human sources (platelets and placenta) are described by Frolik et al in EPO 128,849 (Dec. 19, 1984). Methods for isolating TGF-beta1 and TGF-beta2 from bovine sources are described by Seyedin et al, EPO 169,016 (Jan. 22, 1986), and USSN 129,864, incorporated herein by reference. Other factors within the scope of this invention include, without limitation, transforming growth factor-alpha, beta-thromboglobulin, insulin-like growth factors (IGFs), tumor necrosis factors (TNFs), interleukins (e.g., IL-1, IL-2, etc.), colony stimulating factors (e.g., G-CSF, GM-CSF, erythropoietin, etc.), nerve growth factor (NGF), and interferons (e.g., IFN-alpha, IFN-beta, IFN-gamma, etc.). Synthetic analogs of the factors, including small molecular weight domains, may be used provided they exhibit substantially the same type of activity as the native molecule. Such analogs are intended to be within the scope of the term "bioactive agent," "bioactive substance," and "bioactive additive," as well as within the specific terms used to denote particular factors, e.g., "FGF," "PDGF," and "TGF-beta." Such analogs may be made by conventional genetic engineering techniques, such as via expression of synthetic genes or by expression of genes altered by site-specific mutagenesis. In some cases, such as with PDGF, the factor may be incorporated into the composition in its native form (i.e., in platelets), or as crude or partially purified releasates or extracts. Alternatively, the factors may be incorporated in a substantially pure form free of significant amounts of other contaminating materials.

An "immunomodulatory amount" of factor is an amount of a particular factor sufficient to show a demonstrable effect on the subject's immune system. Typically, immunomodulation is employed to suppress the immune system, e.g., following an organ transplant, or for treatment of autoimmune disease (e.g., lupus, autoimmune arthritis, autoimmune diabetes, etc.). For example, when transplanting an organ one could line the site with the matrix of the invention impregnated with an immunomodulatory amount of an immunosuppresive biological growth factor to help suppress rejection of the transplanted organ by the immune system. Alternatively, immunomodulation may enhance the immune system, for example, in the treatment of cancer or serious infection (e.g., by administration of TNF, IFNs, etc.).

An "oncostatically effective amount" is that amount of growth factor which is capable of inhibiting tumor cell growth in a subject having tumor cells sensitive to the selected factor. For example, many non-myeloid carcinomas are sensitive to treatment with TGF-beta, particularly TGF-beta2, as set forth in copending U.S. patent Ser. No. 928,760, filed Nov. 7, 1986, incorporated herein by reference.

A "hematopoietically modulatory amount" is that amount of growth factor which enhances or inhibits the production and/or maturation of blood cells. For example, erythropoietin is known to exhibit an enhancing activity at known dosages, while TGF-beta exhibits an inhibitory effect.

An "osteoinductive amount" of a biological growth factor is that amount which causes or contributes to a measurable increase in bone growth, or rate of bone growth.

The amount of the factor included in the composition will depend upon the particular factor involved, its specific activity, the type of condition to be treated, the age and condition of the subject, and the severity of the condition. For example, it may be necessary to administer a higher dosage of TGF-beta when treating, for example, adenocarcinoma (e.g., by applying a TGF-beta-containing matrix to the wound after surgical excission of a tumor, before closing) than when simply promoting the healing of a wound (e.g., due to trauma or surgical procedure). In most instances, the factor(s) will be present in amounts in the range of about 3 ng/mg to 30 ug/mg based on weight of collagen.

The addition of heparin to the dispersion has been found to affect the pore size of the implant. When heparin is added the heparin concentration in the dispersion before flash-freezing will normally be between 5 and 300 ug/ml. An "effective amount of heparin" is that amount which provides the desired pore size in the final product matrix.

B. Characteristics of Collagen Implants

Figure 2:
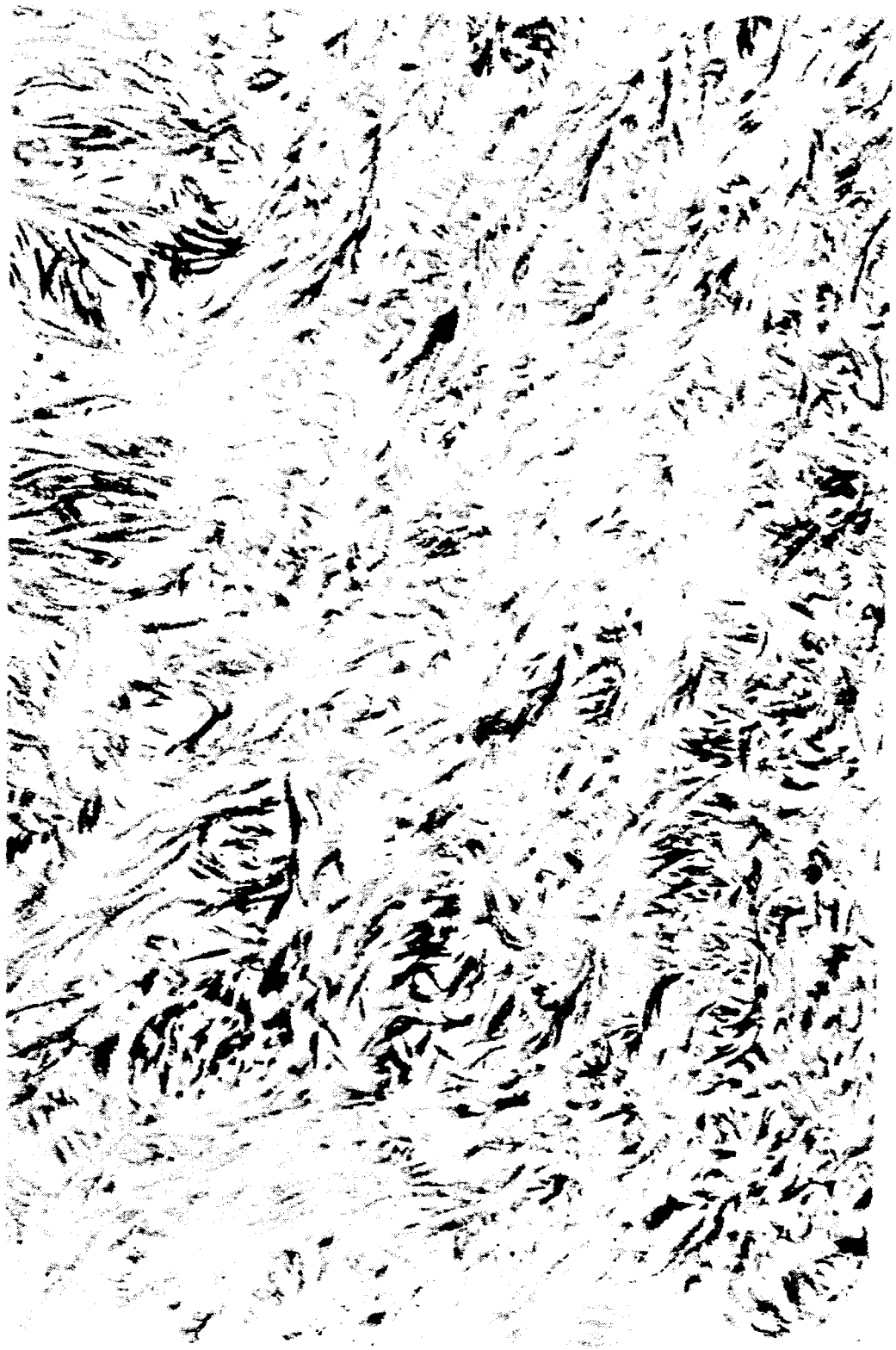
FIG. 2 is a transmission electron microscope photograph of a collagen implant of the invention illustrating the fibrillar structure.

The collagen implants of this invention are coherent nonwoven bodies of collagen fibrils that are characterized by a very consistent, finely fibered structure. FIG. 2 is a transmission electron micrograph of a typical fibrillar product illustrating its fibrillar structure. This structure is further characterized by being made up of fibrils which are essentially uniform diameter circular cross section fibers. The average diameter of these fibrils is normally from about 50 to about 200 nm, more usually from about 100 nm to about 150 nm. Another characteristic of the implants is that they have a bulk density in the range of 0.01 to 0.3 g/cm$^3$.

Yet another characteristic of the implants is that about 80% of the pores of the implant are of a sufficient size to permit cell ingrowth. In this regard at least about 80% of the pore population will have pores of at least 35 microns or greater in diameter, preferably 50 to 250 microns in diameter.

Approximately 1-2% of the heat-treated implant is soluble in acid solution, whereas more than 25% of the non-heat treated implant is soluble.

The fibrous implants will usually be about 2 to about 8 mm thick and are useful as wound healing matrices, surgical dressings, burn dressings and the like. The implants of the invention provide a matrix having the necessary characteristics to permit and encourage healing or promotion of connective tissue deposition, angiogenesis, reepithelialization, and fibroplasia of tissue, even in the absence of additional growth factors. The amount of implant used in wound treatment is typically selected to substantially cover the wound, at a thickness determined by the thickness of the implant material (typically 1-8 mm). The implant may easily be cut to shape in order to fill the wound closely. Where a void is created, e.g., by excision of a tumor or cyst, the implant material may be moistened and packed into the space created.

As indicated previously, the implants are biodegradeable and serve as sustained delivery vehicles for pharmaceutically active (bioactive) substances or other excipients into the implants. These additives may be added to the implant after it is formed, e.g., after lyophilization, or may be incorporated in the casting fluid. For example, one may advantageously incorporate tissue growth factors such as TGF-beta1, TGF-beta2, PDGF-AA, PDGF-AB, PDGF-BB, EGF, acidic FGF, basic FGF, TGF-alpha, connective tissue activating peptides, beta-thromboglobulin, insulin-like growth factors, tumor necrosis factors, interleukins, colony stimulating factors, erythropoietin, nerve growth factor, interferons, and the like. The collagen implant in such formulations releases the incorporated additive over an extended period of time into the site of administration.

The ability of the collagen implants to deliver active substances over a period of time is an important aspect of the invention. The wound healing matrices containing active substances generate a more optimal wound healing response than active substances alone. This response includes persistence of granulation tissue deposition, reepithelialization and vascularization of the wound, and ultimately complete healing of the wound. The matrices of the invention provide several advantages over frequent administration (such as by repeated injection) of active substances alone. These advantages include (1) the ability to maintain the active substance at the treated site over a period of time following each administration, (2) optimal handling properties for the physician, (3) decreased trauma to the patient (e.g., 1-3 treatments per week instead of treatments daily or more), and (4) decreased treatment costs to the patient. Furthermore, the collagen composition of these matrices provides an environment similar to host tissue, encouraging the wound healing response, and is replaced by host tissue as the matrix degrades over time.

EXAMPLES

The invention is further illustrated by the following Examples. These are provided merely to set forth in more detail the practice of the invention, and are not to be construed as a limitation on the scope of the invention.

EXAMPLE 1

Preparation of Collagen Implants

A collagen implant suitable for use as a wound healing matrix is prepared as follows:

Nine (9) parts of flowable viscous Vitrogen ® 100 collagen in aqueous solution, having a concentration of about 3 mg/ml, is precipitated by adding 1.0 part by volume of 0.2 M $Na_2HPO_4$/0.09 M NaOH, pH 11.2 buffer. The amount of base in the buffer is selected to neutralize the acid in the Vitrogen ® 100 solution. The precipitation is carried out at ambient temperature. The precipitate that forms is collected by centrifugation and then homogenized to give a homogenous dispersion. The concentration of protein in the homogenate is then determined and found to be 40-70 mg/ml. A portion of the homogenate is diluted to a collagen concentration of 5 mg/ml with 0.02 M $Na_2HPO_4$/0.13 M NaCl, pH 7.4.

The homogenate is spread on a metal sheet to a thickness of about 5 mm. The metal sheet is then placed in a −80° C. cooler for one hour. This time period is probably longer than needed since the layer is observed to freeze very rapidly under these conditions.

The solid layer so formed is placed in a lyophilizer and allowed to warm to about −20° C. while drawing a vacuum of about 0.01 mm Hg. This is continued for 24 hours, until less than about 25 wt % moisture is present.

The lyophilized layer is then allowed to warm to 15°-20° C. and dried under vacuum for about 8 hours to remove residual free moisture. The implant has a fine homogenous fibrillar structure and is very dense, coherent, and resistant to tearing. This implant is useful as a wound healing implant or as a burn dressing or the like.

EXAMPLE 2

Preparation of Implant with Air

Example 1 is repeated with one change. A volume of the homogenate is placed in a chamber and coupled to a second chamber containing one tenth of its volume of air. The air is injected into the homogenate and the two phases are gently pumped from chamber to chamber until the entire volume of air has been incorporated to give a gas in semisolid dispersion. The dispersion is further processed as in Example 1 to give a solid implant of fibrillar collagen. The implant is less dense than the matrix produced in Example 1, and is easy to tear apart. Although not measured quantitatively, qualitatively it is less strong than the implant of Example 1, that is it is less resistant to tearing. It is also not as stiff as the implant of Example 1. This implant is also useful as a wound healing matrix.

EXAMPLE 3

Preparation of Compressed Implants

The resultant implants made by either of Examples 1 or 2 are further processed by passing individual implant(s) through a roller press to compress each layer into a uniform thickness of about 1 mm. Compressed implants are more dense and more resistant to tearing.

Compressed implants would be used as long-term protective coverings for a wound, while also providing a wound-healing environment.

Preparation of Collagen/Heparin Implants

Medical grade heparin is dissolved in 0.02 M Na$_2$HPO$_4$ buffer, pH 7.8 to a concentration of 500–1,500 ug/ml. The heparin solution is added to a collagen dispersion prepared as in Example 1 but containing 7.5 mg/ml fibrillar collagen to provide dispersions containing 100 ug/ml heparin and 5 ug/ml heparin. The dispersions are then flash-frozen and lyophilized as in Example 1. The resulting collagen-heparin implants are then placed in a vacuum oven and heat-cured at room temperature or 80° C. for 24 hr. Tests were carried out in triplicate.

Mechanical strength of the cured implants was measured using a tension test which determines the rupture strength of wet sponges by pulling with a hanging weight. Dry samples of the implants were cut in 2×1 cm$^2$ pieces and glued to plastic anchor plates using Permabond ® 910 adhesive. The implants were then wetted with phosphate buffered saline for 5 min before clamping down one end of the plastic plate to a stationary board. The clamped sample was stressed with a 20 g hanging weight. The time to break the implant was measured in seconds. This time is referred to as "strength time". Test results are shown in Table 1 below.

TABLE 1

| Sample Composition Before Drying | Treatment | Thickness (mm) | Strength Time (Sec) | Ave. |
|---|---|---|---|---|
| A. 7.5 mg/ml FC | Room Temp. | 2 | 10.0 | |
| 100 ug/ml HP | Vac | 2 | 3.1 | |
| | 24 hrs. | 2 | 18.9 | 11 |
| B. 7.5 mg/ml FC | 80° C. | 2 | 397 | |
| 100 ug/ml HP | Vac | 2 | 77 | |
| | 24 hrs. | 2 | 771 | 415 |
| C. 7.5 mg/ml FC | Room Temp. | 2 | <1 | |
| 5 ug/ml HP | Vac | 2 | <1 | |
| | 24 hrs. | 2 | <1 | <1 |
| D. 7.5 mg/ml FC | 80° C. | 2 | 21.5 | |
| 5 ug/ml HP | Vac | 2 | 170.4 | |
| | 24 hrs. | 2 | 14.1 | 69 |

HP: heparin
FC: fibrillar collagen

The results of Table 1 show that the tear strength of the implants can be increased by heat curing.

Pore sizes of the cured collagen-heparin implants were measured using light microscopy. The pore size results are shown in Table 2 below.

TABLE 2

| Sample Composition Before Drying | Treatment | Ave. Pore Size | Pore Size Range |
|---|---|---|---|
| A. 7.5 mg/ml FC | Room Temp. | 103 ± 63 | 45–282 |
| 100 ug/ml HP | Vac | | |
| | 24 hrs. | | |
| B. 7.5 mg/ml FC | 80° C. | 93 ± 31 | 48–162 |
| 100 ug/ml HP | Vac | | |
| | 24 hrs. | | |
| C. 7.5 mg/ml FC | Room Temp. | 57 ± 19 | 27–109 |
| 5 ug/ml HP | Vac | | |
| | 24 hrs. | | |
| D. 7.5 mg/ml FC | 80° C. | 74 ± 28 | 32–98 |
| 5 ug/ml HP | Vac | | |

TABLE 2-continued

| Sample Composition Before Drying | Treatment | Ave. Pore Size | Pore Size Range |
|---|---|---|---|
| | 24 hrs. | | |

Pore size in microns: all implants 2 mm thick

As shown in Table 2, the amount of heparin added to the implant affects the pore size of the implant.

Modifications of the above described modes for carrying out the invention that are obvious to those of skill in the art of collagen chemistry and/or wound dressings are intended to be within the scope of the following claims.

EXAMPLE 5

Preparation of Collagen/Factor Implant

A collagen/heparin implant containing transforming growth factor-beta (TGF-beta) was prepared as follows:

(A) Preparation of TGF-beta

TGF-beta was prepared as described in U.S. patent application Ser. No. 129,864, filed December 10, 1987. The procedure is as follows:

Bovine metatarsal bone was obtained fresh from a slaughterhouse and transported on dry ice. The bones were cleaned of marrow and non-bone tissues, broken into fragments <1 cm in diameter, and pulverized in a mill at 4° C. The pulverized bone was washed twice with 9.4 l of double distilled water per Kg of bone for about 15 min each, then washed overnight in 0.01 N HCl at 4° C. Washed bone was defatted using 3×3 volumes ethanol, followed by 3×3 volumes diethyl ether (20 min each at room temperature). The resulting defatted bone powder was then demineralized in 0.5 N HCl (25 l/Kg defatted bone) at 4° C. The acid was decanted, and the resulting demineralized bone (DMB) washed with water until the wash pH was greater than 4, followed by drying on a suction filter.

The DMB was then extracted with 3.3 l of 4 M guanidine-HCl, 10 mM EDTA, pH 6.8, 1 mM PMSF, 10 mM NEM per Kg for 16 hours, the suspension suction filtered, and the insoluble material extracted again for 4 hrs. The soluble fractions were combined and concentrated at least 5-fold by ultrafiltration using an Amicon ultrafiltration (10K) unit, and the concentrate dialyzed against 6 changes of 35 volumes cold deionized water over a period of 4 days, and then lyophilized. (All procedures performed at 4° C., except for lyophilization.)

The resulting protein extract was redissolved in 4 M guanidine-HCl, fractionated on a Sephacryl ® S-200 column equilibrated in 4 M guanidine-HCl, 0.02% NaN$_3$, 10 mM EDTA, pH 6.8. Fractions were assayed by their absorbances at 280 nm and their chondrogenic activity (using ELISA to measure the appearance of characteristic proteoglycans in chondrocyte cell culture), and the fractions combined. The fraction exhibiting greatest activity (protein mw 10,000–40,000 daltons) was dialyzed against 6 changes of 180 volumes of deionized water and lyophilized.

The fraction was then dissolved in 6 M urea, 10 mM NaCl, 1 mM NEM, 50 mM sodium acetate (NaOAc), pH 4.8, and centrifuged at 10,000 rpm for 5 min. The supernatant was fractionated on a CM52 column (2.5×20 cm) equilibrated in the same buffer. Bound proteins were eluted from the column using a 10 mM to 400 mM NaCl gradient in the same buffer, and a total volume of 350 ml at a flow rate of 27 ml/hr. The eluate was pooled into three fractions (A, B, and C). Fractions B and C eluted at approximately 150-250 mM NaCl. Each fraction was dialyzed against 6 changes of 110 volumes of deionized water for 4 days, and then lyophilized.

The lyophilized fractions A and BC (combined) were dissolved in 0.1% trifluoroacetic acid (TFA), and aliquots of the solutions applied to a Vydac ® C18 RP-HPLC column (4.6 mm ID×25 cm) and washed with 0.1% TFA for 5 min at 1 ml/min. The eluting solvent was a 0-60% $CH_3CN$ gradient in 0.1% TFA at a rate of 2%/min. Fraction BC provided two peaks: peak 1 at 29.5 min containing TGF-beta1, and peak 2 at 31.2 min containing TGF-beta2.

(B) Preparation of collagen/TGF-beta implant

TGF-beta1 was dissolved in acidic solution (pH 2.0), diluted, and reconstituted with collagen in solution (CIS) to provide a final concentration of 30 ug/ml TGF-beta1 and 300 ug/ml CIS. The solution was then filtered through a 0.22 um Millex ®-GV filter unit to sterilize the protein factor. The sterile TGF-beta1/CIS solution was then mixed with 0.2 M $Na_2HPO_4$ buffer (pH 11.2) to make a storable dispersion containing 27 ug/ml TGF-beta1 and 270 ug/ml CIS.

Medical grade heparin was dissolved in 0.02 M $Na_2HPO_4$ buffer (pH 7.8) to provide a 400 ug/ml heparin solution. One part heparin solution was added to an equal volume of collagen solution (prepared as in Example 1, but containing 30 mg/ml) to provide a collagen/heparin slurry containing 200 ug/ml heparin and 15 mg/ml collagen. One part of this dispersion was mixed with 1 part of the collagen/TGF-beta1 dispersion to provide a final dispersion having 7.6 mg/ml collagen, 100 ug/ml heparin, and 13.5 ug/ml TGF-beta1.

The resulting dispersion was then poured into molds, placed in a Virtis ® SRC15 freeze dryer, and equilibrated to 4° C. The dispersion was then flash-frozen and lyophilized as provided in Example 1.

(C) Similarly, proceeding as in part B above but substituting TGF-beta2 for TGF-beta1, a TGF-beta2/collagen implant of the invention was prepared.

(D) Similarly, proceeding as in part B above but substituting PDGF for TGF-beta1, a PDGF/collagen implant of the invention was prepared.

EXAMPLE 6

Wound Healing in Animal Models

Healing of full thickness wounds in guinea pigs was studied in the following experiment.

The following implant formulations were first prepared:
1. 7.5 mg/ml collagen, 100 ug/ml heparin, 4.0 ug/ml TGF-beta1
2. 7.5 mg/ml collagen, 100 ug/ml heparin, 20 ug/ml TGF-beta1
3. none (control)

The dispersions (1.2 ml) were cast and lyophilized as described above to provide strips 4.5 cm×1.3 cm×0.15 cm.

A midline incision 5 cm long through the cutaneous muscle was made in the dorsal skin of 60 male Hartley guinea pigs. The skin edges were allowed to gape open to form longitudinal lenticular-shaped wounds 5 cm by about 1.2 cm at midpoint, with a mean surface area of 4.2 $cm^2$. Twelve animals were used for each test group. A strip of the test formulation (or control) was inserted in the wound, allowed to hydrate, and molded as necessary to cover the entire base of the defect. The wounds were then covered with Opsite ®, and dressed.

Four animals from each group were studied on days 14 and 21. The wound sites were explanted and examined histologically for epithelialization and deposition of connective and granulation tissue.

The results indicated that at 14 days, wounds receiving implants containing TGF-beta1 were stronger than wounds receiving matrix only. At 21 days, wounds receiving 4 ug TGF-beta1 were significantly stronger than wounds receiving 20 ug TGF-beta1. The results suggest that treatment with TGF-beta1 in collagen/heparin matrix can enhance the strength of open wounds at earlier stages of healing.

EXAMPLE 7

Persistence of Fibrotic Response

The beneficial long-term persistence of the fibrotic response (e.g., connective tissue deposition, fibroplasia, and angiogenesis) induced by the wound healing matrix containing a bioactive agent was studied in the following experiment. The test compositions were prepared as follows:
A: TGF-beta1 (1.5 ug) in PBS (daily injections);
B: TGF-beta1 (10.5 ug) in PBS (bolus);
C: Fibrillar collagen (32 mg/ml)+heparin (300 ug/ml) ("FCH gel");
D: Fibrillar collagen (32 mg/ml)+heparin (300 ug/ml)+TGF-beta1 (10.5 ug);
E: Fibrillar collagen (7.5 mg/ml)+heparin (100 ug/ml) ("matrix");
F: Fibrillar collagen (7.5 mg/ml)+heparin (100 ug/ml)+TGF-beta1 (10.5 ug).

Each formulation additionally contained 500 ug/ml mouse serum albumin (MSA). To prepare the dried collagen matrices, the dispersions of samples E and F were cast and frozen at −40° C. for 2 hours in a lyophilizer. Then, the lyophilization chamber was evacuated and the temperature increased to −20° C. for 24 hours. This lyophilization process was completed by raising the temperature to 20° C. for an additional 24 hours.

Twelve adult female Swiss Webster mice were used in each test group. Group A received sample A by daily injection into the nuchal subcutaneum for 7 days. Groups B, C, and D were injected only on day 1 with the respective test formulations into the nuchal subcutaneum. Groups E and F received their respective test formulations by surgical subcutaneous implantation in the scapular region (the wounds were closed with clips). Explants were taken from each group on days 7, 15 and 30 for histological and morphometric analysis.

Four animals per group were studied at each time point. After 7 days, connective tissue deposition and neovascularization at the administration site were observed in groups that received TGF-beta1. There was a significantly more extensive response in group A (TGF-beta daily), group D (FCH gel+TGF-beta1), and group F (matrix+TGF-beta1), compared to the other groups. After 15 days, administration sites in group F had a significantly greater response than sites in groups B, C, or E. At both day 7 and 15, there were no significant differences between the sites in group A, D, or F. By day 30, there were no significant differences between groups A and D. However, the extent of the response to TGF-beta1 declined steadily in groups A and D, but much more slowly in group F. The data indicates that the persistence of the fibrotic response at subcutaneous sites in adult mice increases when sites are treated with growth factors presented in the collagen matrices of the invention, rather than with growth factors alone.

EXAMPLE 8

Wound Healing Without Factors

The ability of the wound healing matrix without added biological growth factors to enhance healing in dermal wounds was demonstrated in the following experiment. Wound healing normally consists of deposition of granulation tissue (vascular and connective tissue) in the wound defect.

Collagen matrix was formulated containing 7.5 mg/ml of fibrillar collagen, 100 ug/ml heparin, and 0.5 mg/ml of porcine serum albumin.

Lenticular dermal wounds 5 cm in length were created in the skin of domestic pigs. A strip of collagen/heparin matrix (4.5×0.4×0.15 cm) was placed into each of 15 full thickness dermal wounds and hydrated with a few drops of saline. Fifteen similar wounds were left untreated. All wounds were covered with transparent occlusive dressing and gauze sponge, secured with circumferential wrappings of elastic tape. At days 3, 7, and 14, 5 wounds from each treatment group were excised from the animal and examined with histomorphometrical techniques.

At all times, the mean amount of granulation tissue in the wounds treated with matrix was significantly greater than in untreated wounds ($F(2,30)=19.4$, $p=0.0001$). In particular, at day 7, granulation tissue was greater in the matrix treated wounds ($F(1,30)=32.0$, $p<0.005$).

The data demonstrates that the collagen matrix enhances wound healing even in the absence of additional factors, by stimulating the deposition of increased amounts of granulation tissue in the wound.

What is claimed is:

1. A method for promoting wound healing of a wound of a human subject, comprising the steps of:
    topically applying to the wound of the human subject a matrix having a density of about 0.01 to about 0.3 g/cm$^3$, a thickness of about 1–20 mm, and pores at least 80% of which are at least 35 μm in diameter, wherein said matrix comprises:
    fibrillar atelopeptide collagen, wherein said fibrils are about 50–200 nm in diameter, and are not chemically crosslinked;
    a pharmaceutically effective amount of a biological growth factor; and
    allowing the matrix to remain in contact with the wound for a period of time sufficient for the growth factor to promote wound healing.

2. The method of treatment as claimed in claim 1, wherein the biological growth factor is selected from the group consisting of TGF-β including β1 and β2 forms, PDGF-AA, PDGF-AB, PDGF-BB, EGF, acidic FGF, basic FGF, TGF-α, connective tissue activating peptides, β-thromboglobulin, insulin-like growth factors, tumor necrosis factors, interleukins, nerve growth factors and interferons.

3. The method as claimed in claim 2, wherein the biological growth factor is a TGF-β.

4. The method as claimed in claim 3, wherein the TGF-β is TGF-β1.

* * * * *